United States Patent [19]

Fischell

[11] 4,295,474

[45] Oct. 20, 1981

[54] RECORDER WITH PATIENT ALARM AND SERVICE REQUEST SYSTEMS SUITABLE FOR USE WITH AUTOMATIC IMPLANTABLE DEFIBRILLATOR

[75] Inventor: Robert E. Fischell, Silver Spring, Md.

[73] Assignee: The Johns Hopkins University, Baltimore, Md.

[21] Appl. No.: 81,167

[22] Filed: Oct. 2, 1979

[51] Int. Cl.³ .............................................. A61B 5/04
[52] U.S. Cl. ............................... 128/697; 128/419 D
[58] Field of Search ............................... 128/695–697, 128/710–712, 419 D, 419 P, 419 PG, 419 PS, 419 PT; 346/33 ME

[56] References Cited

U.S. PATENT DOCUMENTS

| | | | |
|---|---|---|---|
| 3,799,148 | 3/1974 | Rowen | 128/711 |
| 4,098,267 | 7/1978 | Stein et al. | 128/712 |
| 4,140,131 | 2/1979 | Dutcher et al. | 128/419 PT |
| 4,223,678 | 9/1980 | Langer et al. | 128/419 D |

*Primary Examiner*—William E. Kamm
*Attorney, Agent, or Firm*—Robert E. Archibald

[57] ABSTRACT

The invention relates to a system and apparatus, particularly adapted for use with an automatic implantable defibrillator, for monitoring electrocardiagram (ECG) data signals to provide a continuously updated recording of the ECG data. The proposed recorder responds to the operating condition of the automatic implanted defibrillator device and places into storage, for subsequent readout by the patient's doctor, ECG data both immediately preceding the onset of a ventricular fibrillation episode and also during the subsequent defibrillation activity, when one or more high energy electrical impulses are applied to the patient's heart. Selected other data regarding operation of the implanted defibrillator and pertinent to the doctor's evaluation of the patient's condition as well as the efficacy of the defibrillator unit, are also recorded by the proposed apparatus for subsequent readout. In addition, the proposed recording apparatus operates to automatically alert the patient that ventricular fibrillation has been detected and that defibrillation is to be attempted, so that appropriate precautions may be taken. Moreover, following defibrillation, the patient is alerted in a distinctive manner that defibrillation has occurred and that a physician should be contacted, as soon as possible.

34 Claims, 14 Drawing Figures

RECORD TIMING

READOUT TIMING

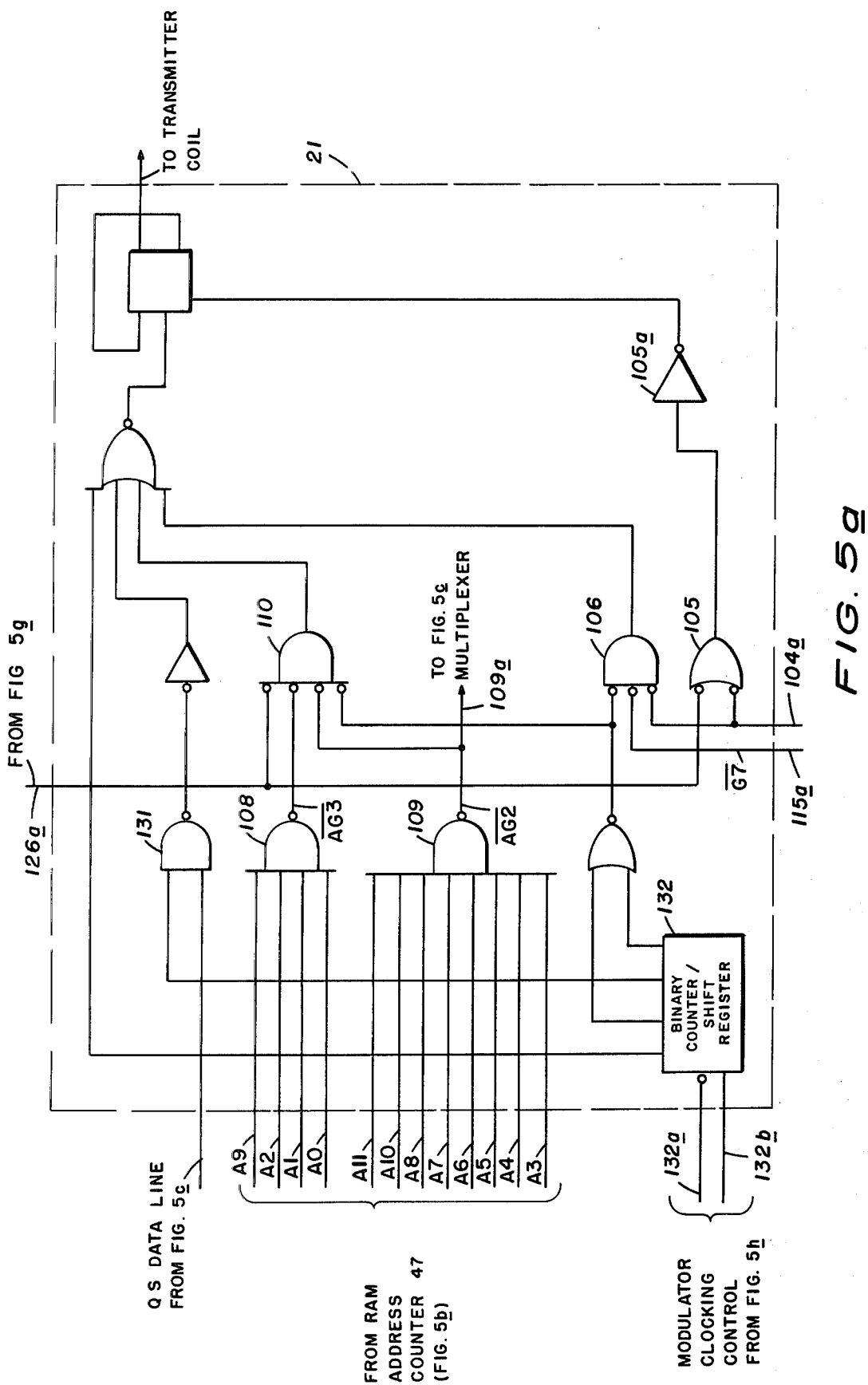

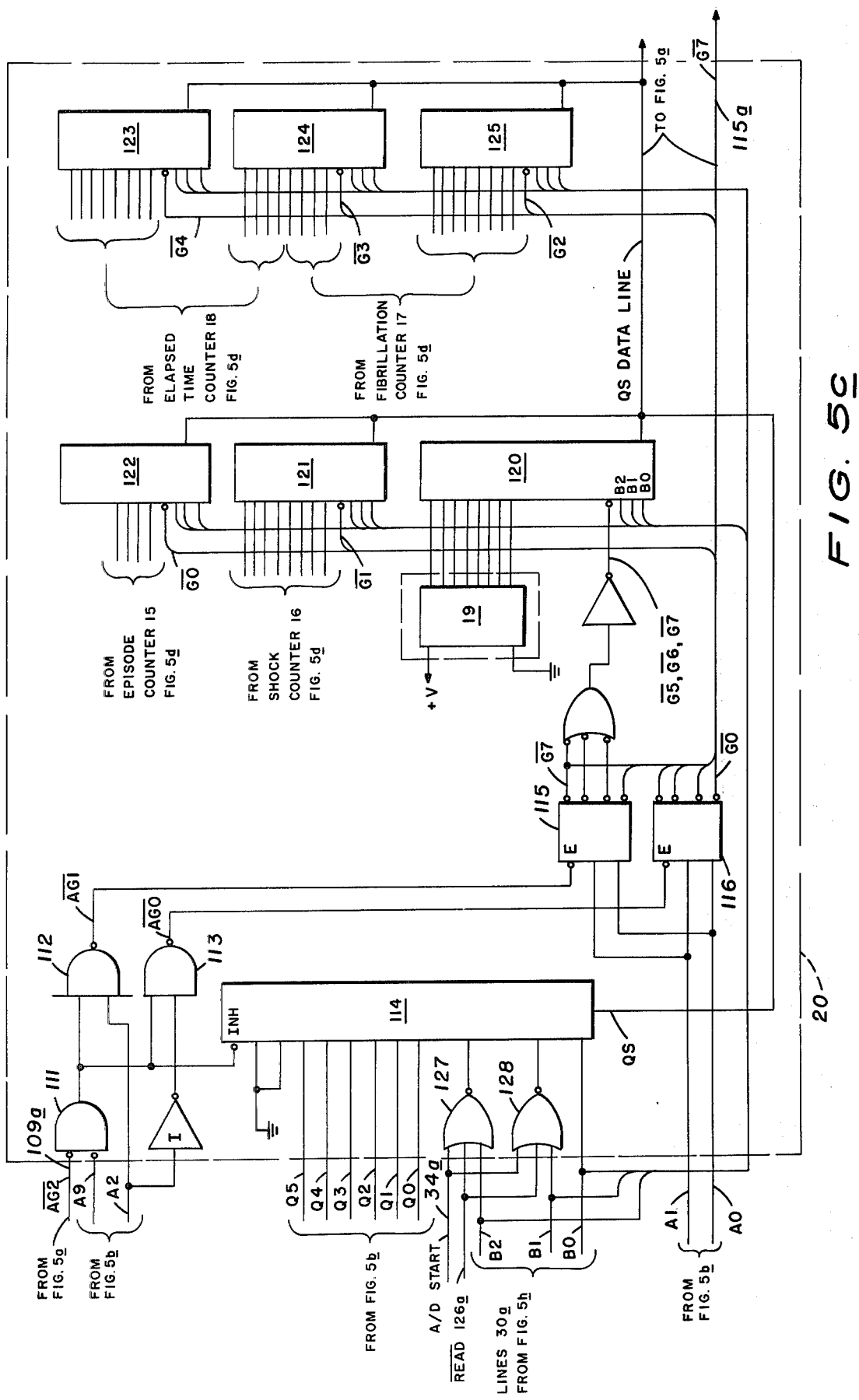

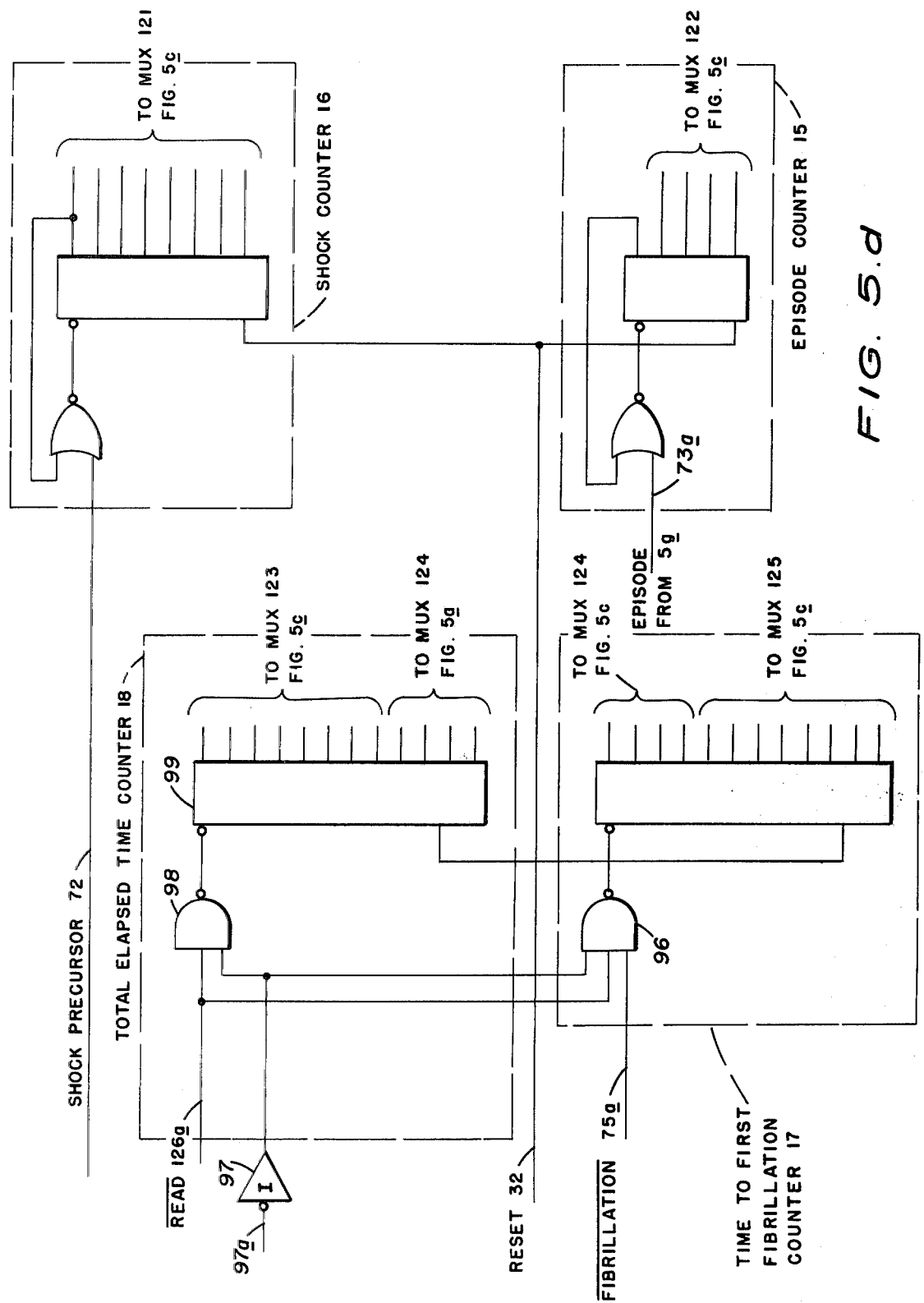
FIG. 5.d

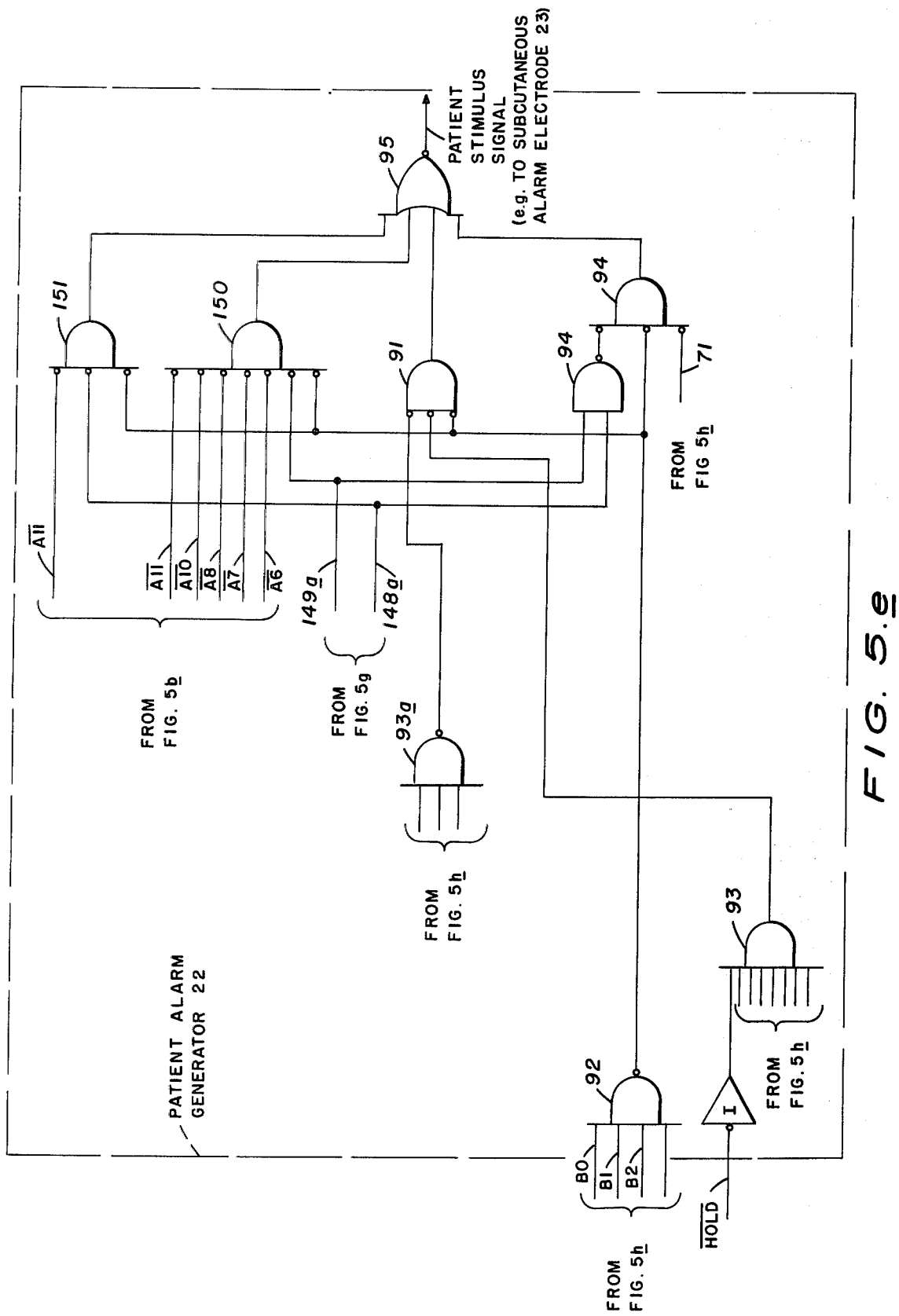
FIG. 5.e

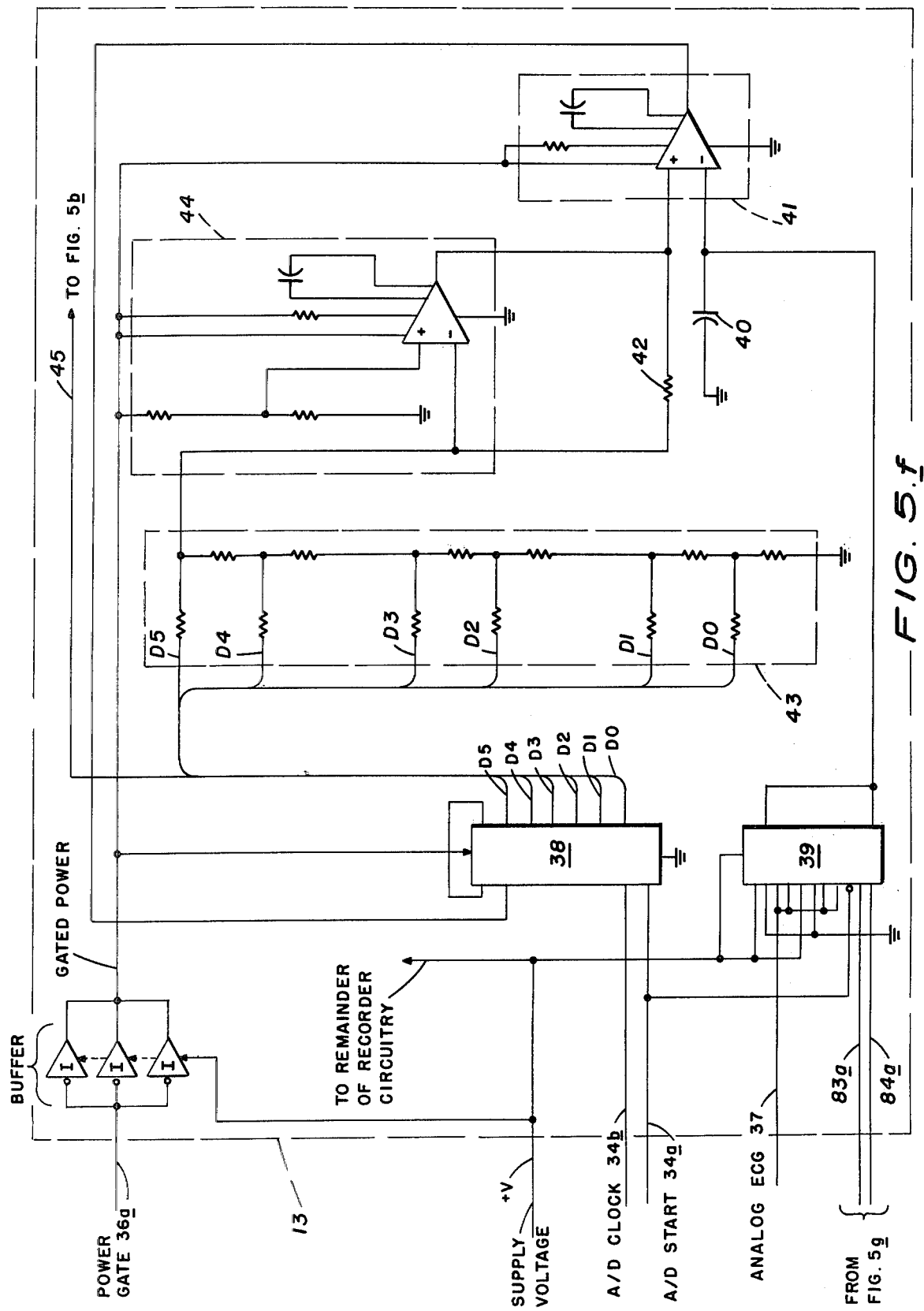
FIG. 5.f

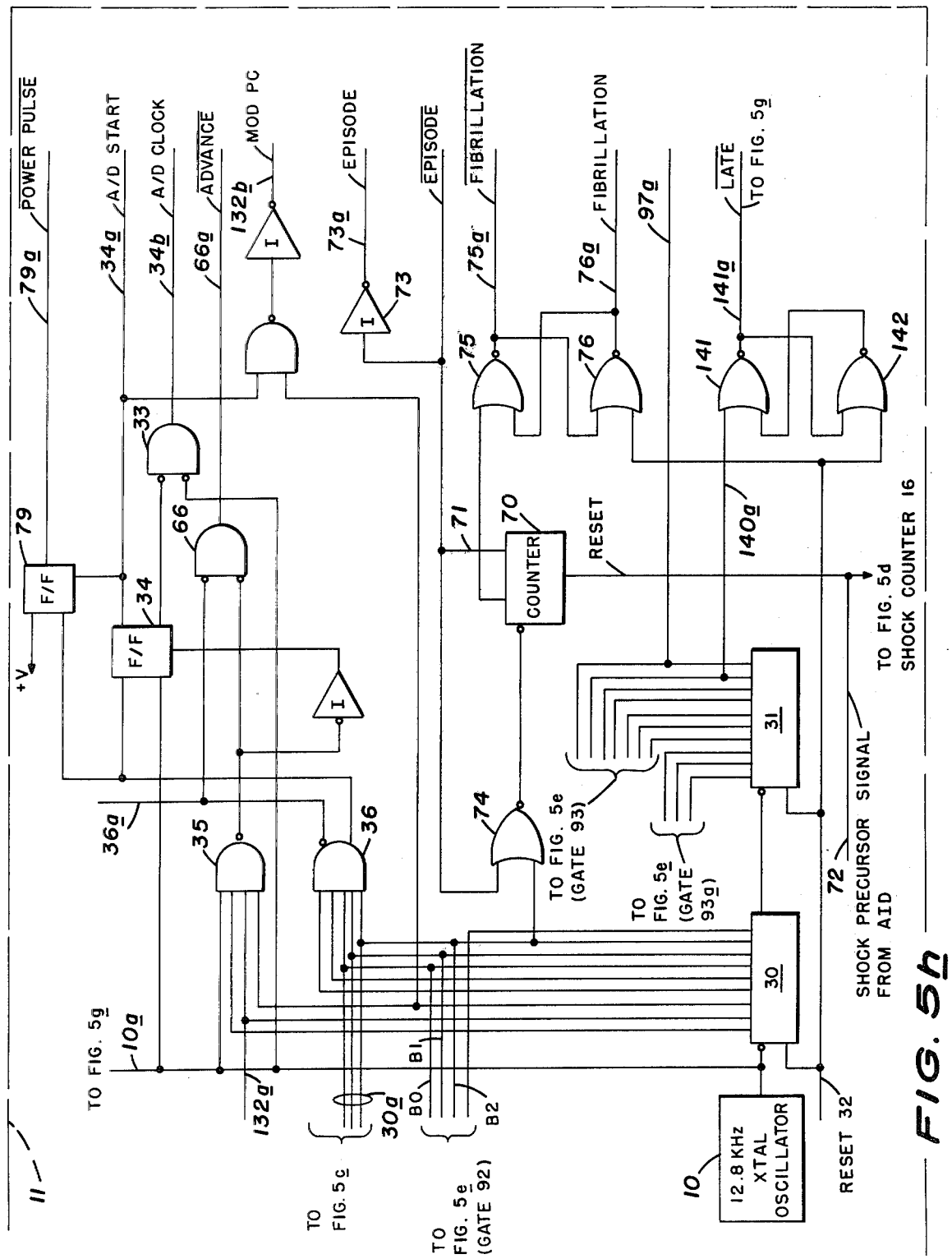

RECORDER WITH PATIENT ALARM AND SERVICE REQUEST SYSTEMS SUITABLE FOR USE WITH AUTOMATIC IMPLANTABLE DEFIBRILLATOR

BACKGROUND OF THE INVENTION

A totally implantable and automatic defibrillator device has been proposed previously by M. Mirowski et al, and is disclosed in reissue patents, U.S. Pat. Nos. Re. 27,652 and 27,757. The implanted automatic implantable defibrillator (AID) device responds to the detection of cardiac malfunction; e.g. ventricular fibrillation, and automatically applies one or more high-energy defibrillation impluses to the heart. Thus, the patient's heart function is monitored by means which discriminate between normal and abnormal heart functioning and when an abnormal condition is detected, i.e. when fibrillation is occurring, a storage capacitor within the defibrillator unit is charged to a high voltage level, and is subsequently discharged as a defibrillation impluse applied to the patient's heart, unless the heart resumes normal functioning within a preselected time interval. If the initial defibrillation impluse fails to return the patient's heart to normal functioning, provision is made for automatically applying several additional defibrillation impluses.

SUMMARY OF THE INVENTION

As previously mentioned, the proposed recording apparatus of the present invention is intended for use with an implanted automatic defibrillator, for example, for monitoring inter alia the patient's ECG data in order to provide a record of the condition which initially caused the activation of the defibrillator device and the application of one or more defibrillation impluses to the patient's heart. As will be described in more detail hereinafter, this recorded information will greatly assist the patient's physician in diagnosing the patient's cardiac problems. Moreover, in accordance with the present invention, the proposed recorder also records ECG data during the defibrillation attempt and thus serves to verify the operation of the implanted defibrillator device, as well as the patient's response. The proposed recorder is designed to permit readout to the patient's doctor, on command, e.g. when the patient visits the doctor's office or a hospital or other medical center.

It is also proposed in accordance with the present invention that a separate alarm apparatus will, in response to the sensing that fibrillation has occurred, provide the patient with an appropriate early warning or alarm, so that the patient may take appropriate precautionary steps to minimize the dangers associated with ventricular fibrillation. More specifically, when a patient experiences ventricular fibrillation, an unconscious state will normally ensue somewhere between five and fifteen seconds subsequent to the onset of fibrillation, due to a lack of oxygen to the brain. Accordingly, if the patient is involved in an activity, such as driving an automobile or standing, when the onset of fibrillation occurs, it is imperative that warning be given of the impending unconsciousness, so that appropriate action can be taken by the patient to decrease the probability that he will hurt himself when he becomes unconscious. Moreover, in accordance with the present invention, the proposed system includes provision for providing the patient with a service request alert following successful defibrillation indicating that a cardiac abnormality and subsequent defibrillation have occurred so that, as soon as possible, the patient will visit his doctor for examination.

In view of the above discussion, one object of the present invention is to provide recorder system/apparatus capable of being used in conjunction with an implantable automatic defibrillator unit, to provide a reliable recording of the patient's ECG data both immediately prior to and during a fibrillation episode/defibrillation attempt sequence.

A further object of the present invention is to provide an alarm apparatus incorporating a patient warning feature, whereby the patient is alerted to the onset of cardiac abnormality, e.g. ventricular fibrillation, and of an impending defibrillation attempt and is also alerted by means of a service request alert, following successful defibrillation, that medical attention should be obtained as soon as practical.

A further object of the present invention is to provide recorder apparatus amenable to microminiturization through the use of digital logic circuitry, with low power requirements, and therefore adaptable for implantation along with the automatic defibrillator device if desired.

A further object of the present invention is to provide patient-carried recorder apparatus which can be read out, on command, during visit to the doctor's office, in order to enable to doctor to analyze the patient's ECG data corresponding to the cardiac activity which caused an implanted automatic defibrillator unit to operate and also to the cardiac activity which occurred during the defibrillation attempt. Such recorded information would be very valuable to the doctor in diagnosing the patient's problem, in order to provide more effective treatment, and would also assist the doctor (and the technical engineering personnel concerned with defibrillator design) in recognizing improper operation of the implanted defibrillator unit.

A further objective of the patient-carried apparatus is to provide audio and/or visual indications to the patient that will serve as the patient alarm and service request alert that have been described herein.

Other objects, purposes and characteristic features of the present invention will in part be pointed out as the description of the invention progresses and in part be obvious from the accompanying drawings wherein.

Figures 6, 7:
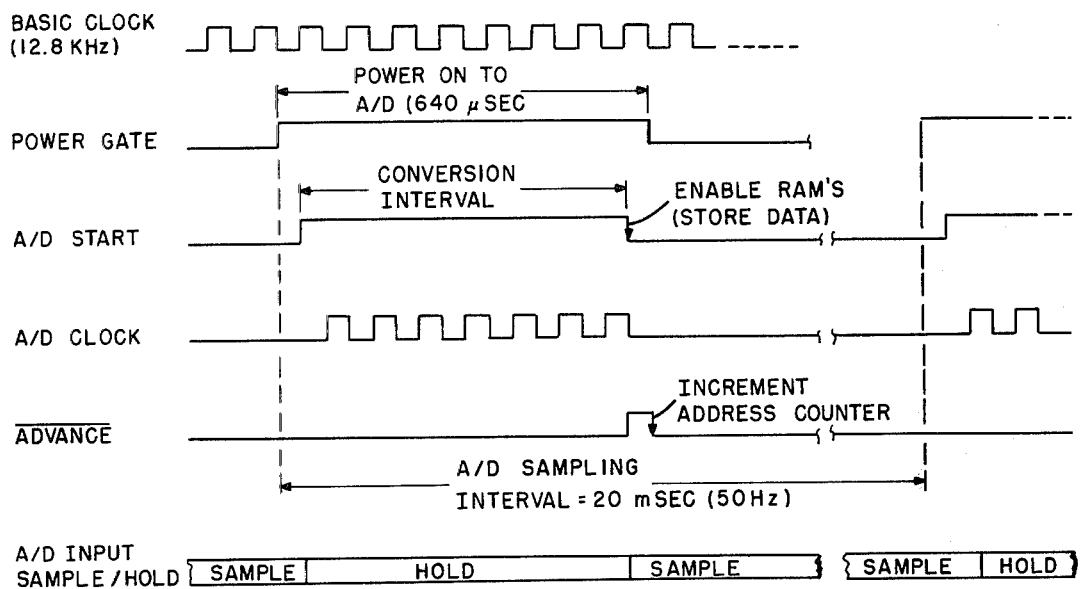

FIG. 5a through 5h form a detailed schematic diagram of the illustrated embodiment employing digital logic circuitry;

FIG. 6 is a timing diagram associated with the conversion of analog ECG data into digital data format; and FIG. 7 is a truth table illustrating the generation of sequential timing signals used in multiplexing stored data during readout from the recorder.

GENERAL OPERATION

Figure 2:
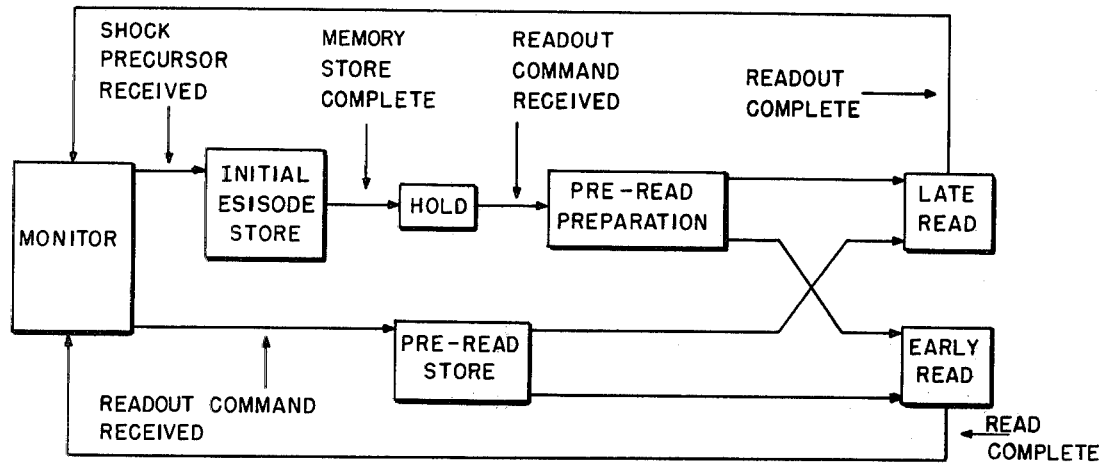
FIG. 2 is a diagrammatic illustration of the various operating modes or states of the proposed recorder.

Before beginning a detailed description of the structure and operation of the proposed recorder system, a general understanding of the present invention may be obtained by reference to the operational mode or state diagram shown in FIG. 2. During the period between visits to the doctor, when no fibrillation episode has yet occurred, the recorder remains in the illustrated MONITOR state. In this condition a small, dedicated (referred to as "precursor") portion of recorder memory is used to preserve a ten-second record of normal ECG data for reference and comparison. The amount of ECG data thus recorded could, of course be longer or shorter than 10 seconds. New data is continuously being written into this "precursor" memory portion so that, at any given time, the latest (typically) ten second period of ECG information is present in the recorder memory. When the proposed recorder is being utilized in combination with an automatic implantable defibrillator (AID) unit, the patient's ECG data signal being monitored by the recorder is being applied simultaneously as input to the AID unit.

If a fibrillation condition occurs, a shock precursor signal (originating in the AID, for example) is received by the proposed recorder system and switches it from the MONITOR state to the INITIAL EPISODE STORE state. At this point, two things happen: an "alarm" signal is generated (see FIG. 3) to warn the patient that cardiac abnormality has occurred and that a defibrillation impulse or shock, or set of shocks, is about to occur; and secondly, a continuous recording of ECG data is begun in the remaining larger portion of memory (e.g. seventy seconds) not used for precursor data storage. This preserves the next seventy seconds (or more or less time) of ECG data encompassing the entire defibrillation attempt; i.e. time period required for the maximum number of impluses contained in one defibrillation attempt or a sequence of attempts. No more data may be stored in the precursor memory portion once a fibrillation detection has occurred, so the total memory now contains eighty seconds of ECG data, covering both the period (typically, 10 sec.) just prior to onset of fibrillation and the period (typically 70 sec.) of fibrillation/defibrillation attempt sequence.

Once the recorder's memory has been filled with data from this initial fibrillation/defibrillation episode, the recorder enters a HOLD state. Further writing of ECG data into memory is inhibited, and a "service request" alert or stimulation is generated to prompt the patient to visit his doctor. This "service request" alert, which has a characteristic distinct from the "alarm" signal previously mentioned, is preferably repeated at regular intervals (e.g. every 45 minutes) until the visit to the doctor is made. If additional fibrillation episodes should occur during the HOLD state, a record is kept in other recorder circuitry of both the number of episodes and the number of defibrillation impulses shocks applied in response. A time-line representation of the three states discussed above is given in the upper half of FIG. 3.

At the doctor's office provision is made, e.g. by means of a readout command or control magnetic coil placed over the implanted defibrillator/recorder, for the doctor to communicate a "readout command" to a magnetic switch for example contained in the recorder device. This places the recorder into its illustrated PRE-READ PREPARATION state—a 70 second interval (see lower portion of FIG. 3) during which the recorder transmits an initializing block of pulses (all zero's) to allow an external receiver to synchronize to the recorder clock rate. Toward the end of this sequence, a frame-synchronization modulation pattern is also generated to mark the beginning of real data.

At this point, the recorder is switched to one of two READ states. Normally, i.e. where it has been more than a preselected time interval (e.g. ten minutes) since the last attempt to read data from the recorder, this will be the LATE READ state; whereas, the EARLY READ state is associated with readout sequences less than ten minutes apart. Once a READ state is entered, the recorder will read out all data at least two times (eighty seconds per readout) to allow the doctor's receiving equipment to verify the data integrity, for example, even if the command magnetic coil is removed immediately after the magnetic read command switch is operated. In this case, completion of the second readout will cause all event counters within the recorder to be reset, as will be described later, and the recorder will revert to the MONITOR state. If more than two readouts are desired, the readout command coil is left in place until all desired information has been received. When the readout command means is finally removed, the recorder will immediately change to the MONITOR state and all internal counters will be reset. Readout timing for the sequence just described is shown in the lower half of FIG. 3.

Even if no fibrillation episodes have occurred, a routine visit to the doctor may be used to test the proposed recorder apparatus and the associated AID unit. In this case, placement of the readout command coil over the device causes the recorder to change from the MONITOR state to the PRE-READ STORE state in which operation is similar to the INITIAL EPISODE STORE mode, in the sense that patient ECG data is then stored in the larger or main portion of memory for a period of seventy seconds. However, this state also resembles the PRE-READ PREPARATION state since it provides a pulse stream of zero's which is transmitted to the external receiver for synchronization purposes. At the end of this seventy-second store/preparation operation, the recorder enters the LATE READ state and transmits data as previously described. Again, transmission of a minimum of two readout cycles is preferable.

Additional testing may be performed by the patient's physician, involving the illustrated EARLY READ state of the proposed ECG recorder. More particularly, the recorder will pass from the MONITOR and PRE-READ STORE states to the EARLY READ state if a read command is initiated within ten minutes of the time the recorder enters its MONITOR state; thus allowing the doctor to obtain an additional readout of normal ECG shortly after one of the readout sequences previously described. It is also possible in this EARLY READ state to generate a test sequence of "alarm" and "service request" signals, in order to acquaint or remind the patient of their characteristics. Thus, for example, if the readout command coil is put in place and then removed shortly thereafter, two readout cycles will be transmitted, and one "alarm" signal followed by a "service request" signal will be generated. If only an ECG record is desired, leaving the readout coil in place longer than the two-readout time span will prohibit the generation of the patient the alarm and service request signals. It will be obvious to someone skilled in the art that the "alarm" and "service request" signals can take various forms; e.g. an audible alarm when the entire apparatus is external, or (as in the preferred embodiment) a mild subcuntaneous electrostimulation which produces a tickle sensation which can be readily detected by the patient and could even be programmed to be painful.

SYSTEM BLOCK DIAGRAM

Figure 1:
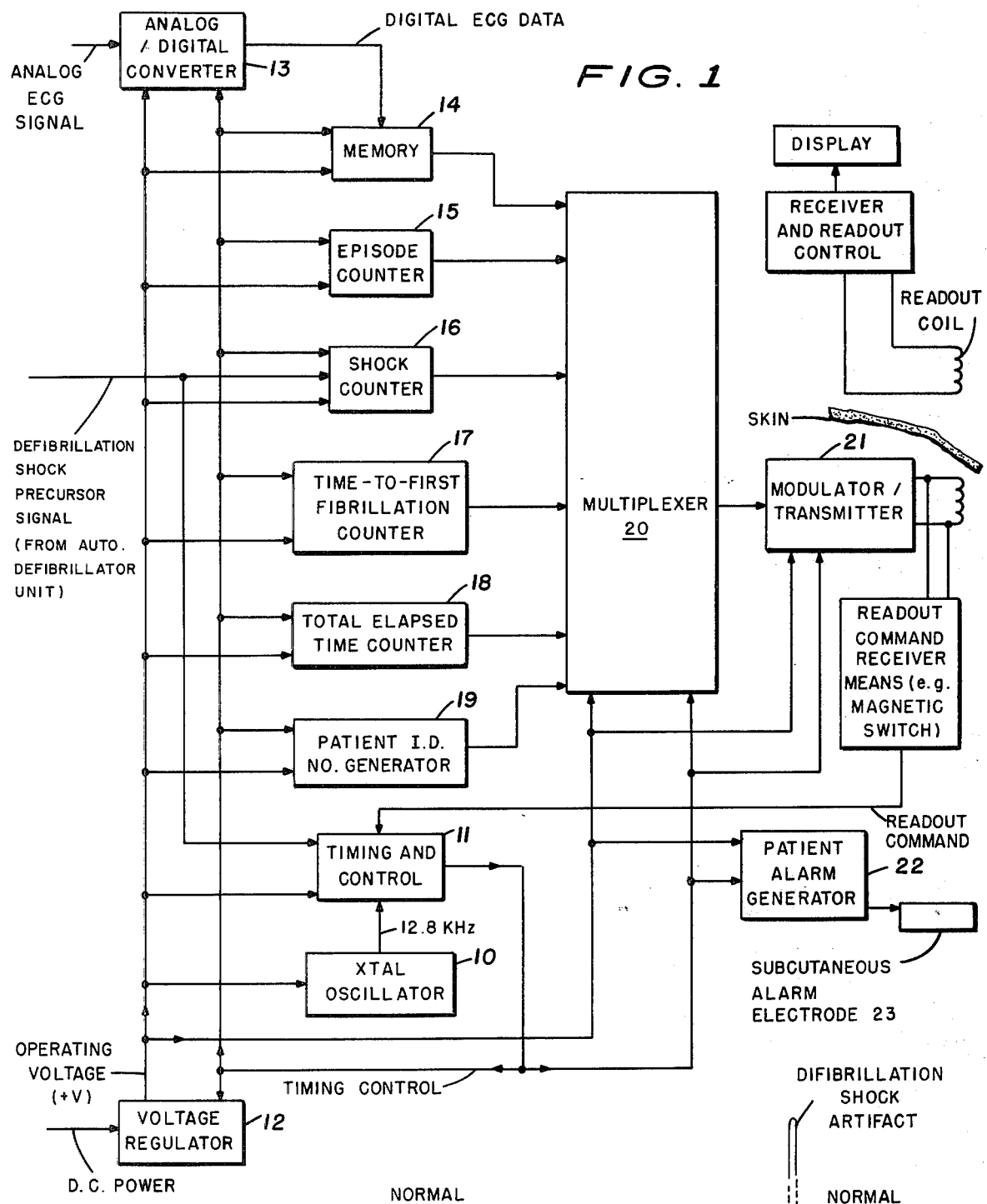
FIG. 1 is a block diagram of a recorder system constituting one embodiment of the present invention.

A generalized block diagram of an implantable embodiment of the proposed recorder system is shown in FIG. 1 and includes a crystal oscillator 10, of conventional design, which provides stable clock pulses, e.g. at 12.8 kHz, for the timing chain and logic control functions (represented at block 11) to be described later. Input DC power, at the desired voltage, is furnished via voltage regulator 12 from a suitable battery supply, for example, (not shown) which preferably would be rechargeable where the proposed recorder system is intended for implanted use.

The proposed recorder system is operably connected to receive and monitor the patient's analog ECG waveform and convert it, at 13, to a suitable, multi-bit digital format. For example, in one practical application, the analog/digital converter 13 converts the input analog ECG data into a six-bit code. This digital ECG data is then stored in memory 14. Also, in order to reduce average power dissipation, power to the analog/digital converter 13 is preferably turned on only during the time that an ECG data sample is being converted and stored in memory 14. All other circuits may be continuously powered.

As indicated in FIG. 1, the proposed recorder system also includes various counter circuits for keeping track of the occurrence of selected events; that is, an episode or event counter 15 maintains a record of the number of fibrillation events which have been detected between readouts; a shock counter 16 records the total number of defibrillation shocks applied during the same interval; a time-to-first fibrillation counter 17 which records the elapsed time from the last readout to the initial fibrillation episode; and, a total elapsed time counter 18 which provides a measure of the time elapsed since the last readout and which also allows a check of timing circuit reliability in the recorder. The details of these counter units will be described hereinafter.

A device identification (ID) number generator 19 is also included, for inserting a fixed pattern tag in the data stream, during readout, to aid in subsequent record keeping. The multiplexer 20 organizes the contents of the memory 14 and the various counters 15-18, as well as the ID tag, into a serial output data stream which is applied to a modulator/transmitter unit 21 where the data are coded in such a manner that it can be recovered by the illustrated external receiving equipment without transmitting a separate clock signal.

The proposed apparatus also includes a patient alarm generator unit 22 which is connected to a suitable subcutaneous stimulation alarm electrode 23, for example, or similar signalling apparatus and which functions, as will be described, to furnish patient-alert signals to warn the patient that fibrillation is occurring (and that unconsciousness and a defibrillation attempt will follow) and, subsequently, that successful defibrillation has occurred so that visitation will be made promptly to the patient's doctor (i.e., the service request alert).

Figure 4:
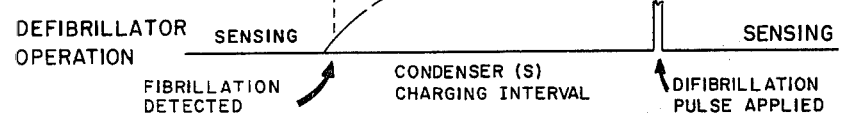
FIG. 4 is a waveform diagram illustrating the typical operation of an automatic implantable defibrillator (AID) unit in response to detected fibrillation of the patient's heart and as associated ECG signal.

As noted previously, the proposed recorder system of the present invention is particularly suited for use with an automatic implantable defibrillator, such as that disclosed in reissue patents, U.S. Pat. Re. Nos. 27,652 and 27,757, wherein a storage capacitor(s) is connected to a battery power supply via DC/DC conversion circuitry. A sensing circuit, responsive to intraventricular pressure for example or to the patient's ECG signal, senses when the patient's normal cardiac rhythm ceases with the onset of fibrillation (See FIG. 4) and the storage capacitor begins charging. If the patient's cardiac activity remains in a fibrillation state for more than a preselected time period, the storage capacitor voltage is discharged into the patient's heart (as denoted in FIG. 4 by the DEFIBRILLATION PULSE) one or more times, as needed, to trigger or shock the heart back into normal rhythm. In accordance with the present invention the proposed recorder system is also responsive to patient's ECG signal and, in addition, receives input from the defibrillator unit indicating each time a defibrillation impulse or shock is applied.

DETAILED DESCRIPTION OF ILLUSTRATED EMBODIMENT

The details of one embodiment of the proposed recorder system are illustrated in FIGS. 5a through 5h of the accompanying drawings, implemented with a discrete digital logic circuitry. More specifically, the basic timing chain for the illustrated embodiment (see FIG. 5h) employs a base 12.8 kHz clock generated at crystal oscillator 10 and applied to a pair of serially connected binary counters 30 and 31 which operate to divide down the base clock frequency into the various timing and control logic signals utilized in the illustrated embodiment. These two counters 30 and 31 also receive a RESET input on line 32, as will be described hereinafter.

CONVERSION AND STORAGE OF ECG SIGNAL

The basic 12.8 kHz clock signal from oscillator 10 is also applied as input to AND gate 33; flip-flop circuit 34 and AND gate 35 (see FIG. 5h) which operate together to produce A/D START and A/D CLOCK control signals on lines 34a and 34b for controlling operation of the analog-to-digital converter circuitry shown in FIG. 5f. In addition, the AND gate 35 receives input from the first three stages of the counter unit 30 and thus provides output pulses at a 1.6 KHz rate; i.e. 12.8 KHz $\div 2^3$. Similarly, the next five higher stages of the counter 30 are applied to AND gate 36 to generate a 50 Hz power gating pulse at the output line 36a leading to FIG. 5f effective to turn on the A/D converter circuitry to digitize the analog ECG (input on line 37 in FIG. 5f) at a 50 Hz rate, with each power gate pulse being 640 microseconds in width (see FIG. 6). In other words, the analog ECG signal is sampled fifty times per second, and during each 640 microsecond sampling interval, the A/D converter circuitry of FIG. 5f converts the analog ECG signal on line 37 to a corresponding six-bit digital code (lines D0 through D5 in FIG. 5f).

More particularly, the power gate signal generated on line 36a in FIG. 5h is applied as control input to a successive approximation register 38, of conventional design, which is presettable to one-half of a predetermined reference voltage level. As a result, only during the power gate pulse is the successive approximation register 38 allowed to function to perform the A/D conversion of the input analog ECG signal. Accordingly, any significant power drain represented by the A/D converter circuitry is caused to exist only when absolutely necessary; i.e. when the ECG signal is being converted to digital form. The register 38 also receives, as input, the A/D CLOCK signal on line 34b which is generated by the AND gate 33 in FIG. 5h at the basic 12.8 kHz clock rate, by connecting the basic clock signal and the output of F/F circuit 34 as inputs thereto. The A/D START signal on line 34a is supplied to the successive approximation register 38 of FIG. 5f in the form of a positive pulse generated by F/F circuit 34 (see FIG. 5h) in response to the basic timing clock and the non-inverted output of the power gate AND circuit 36.

The A/D START signal on line 34a is also applied, in FIG. 5f, to a multiplexer circuit 39 along with the analog ECG signal 37 received, for example, from the same sensing and impluse electrode utilized by the implanted defibrillator device. The multiplexer unit 39, in combination with capacitor 40, functions as a sample and hold circuit connected at the negative (−) input of a comparator circuit 41. The positive (+) side of the comparator 41 is connected through resistor 42 to one side of a resistor ladder network 43 which operates together with an amplifier circuit 44 to perform D/A conversion on the output of the successive approximation register 38, so that it may be compared, at comparator 41, with the ECG analog input on line 37. More specifically, in accordance with the application of the A/D CLOCK signal to the successive approximation register 38, the input analog ECG signal 37 is compared sequentially with a variable reference voltage level from the resistor network 43; e.g. the register 38 is set initially (during bit position D5) to cause one-half of a maximum reference voltage from resistor ladder 43 to be compared, at 41, against the input analog ECG signal and, depending upon the output of the comparator 41, the bit position (D5) is set at either a binary one or zero. During the next successive bit position (D4), the reference voltage used during the first step is either increased or decreased by half and a second comparison step made. This process is repeated for the subsequent bits D3, D2 etc. until the final output binary code from the register 38 (shown here as a six-bit digital code on lines D0 through D5) represents a successive approximation of the input analog ECG signal.

Figure 5B:
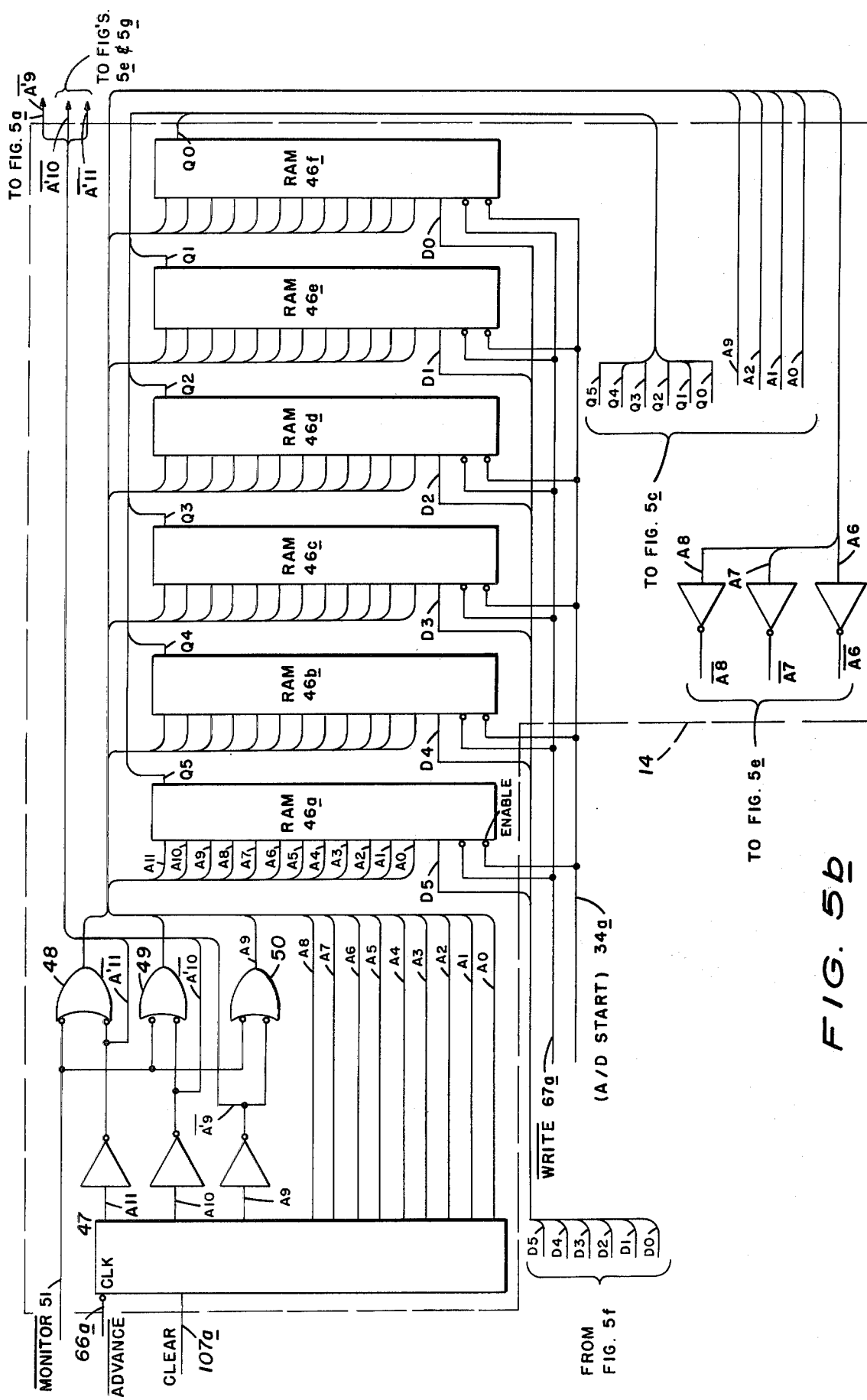

This six-bit digital ECG code is then applied, along line 45, to the memory portion 14 of the recorder shown in detail in FIG. 5b of the drawings. More particularly, the illustrated memory comprises six random access memories (RAMs) designated at 46a through 46f in FIG. 5b, with the most significant bit (D5) being applied to RAM 46a and the least significant bit (D0) being applied to RAM 46f. In one practical application of the proposed recorder system, each RAM comprises a memory which is one bit wide and 4K bits deep; i.e. only a single bit position of the digital ECG code is assigned to each RAM stage. As also illustrated in FIG. 5b, the A/D START signal is applied as an enable signal to the RAM stages, so that the digital ECG code is stored into memory on the trailing edge of the A/D START pulse signal (see FIG. 6).

A RAM addressing counter 47 is provided to control both storage and readout of the ECG digital code. Storage occurs either in the main, lower levels of the RAM memory in FIG. 5b, corresponding to seventy seconds of ECG data encompassing a defibrillation attempt, or in the remaining upper RAM memory levels which corresponds to a ten second interval and which are reserved for storing updated ECG data immediately preceeding the onset of fibrillation. Specifically, the upper ten second portion of the memory is addressed so long as the recorder is in its MONITOR state (see FIG. 2); i.e., the three OR gate circuits 48, 49 and 50 in FIG. 5b respond to the $\overline{\text{MONITOR}}$ control voltage level on line 51 and force a binary one on address lines A9, A10 and A11 (MSB), to maintain the RAM's in their upper (ten second) storage condition whenever the recorder is in its MONITOR state or condition. As a result, the RAM address counter 47 continuously circulates the RAM's 46a–f through their uppermost one-eighth portion to provide the most recent ten seconds of ECG data prior to the onset of fibrillation. When, however, the control signal on line 51 goes high (to indicate that the recorder has been actuated out of its MONITOR state) the OR gates 48, 49 and 50 are released to respond to the counter 47 and to write the subsequently occurring ECG data into the remaining lower seven-eighths of the memory corresponding to seventy seconds of ECG data encompassing the fibrillation/defibrillation attempt sequence, as will be described.

RECORDING OF INITIAL FIBRILLATION EVENT

Figure 5G:
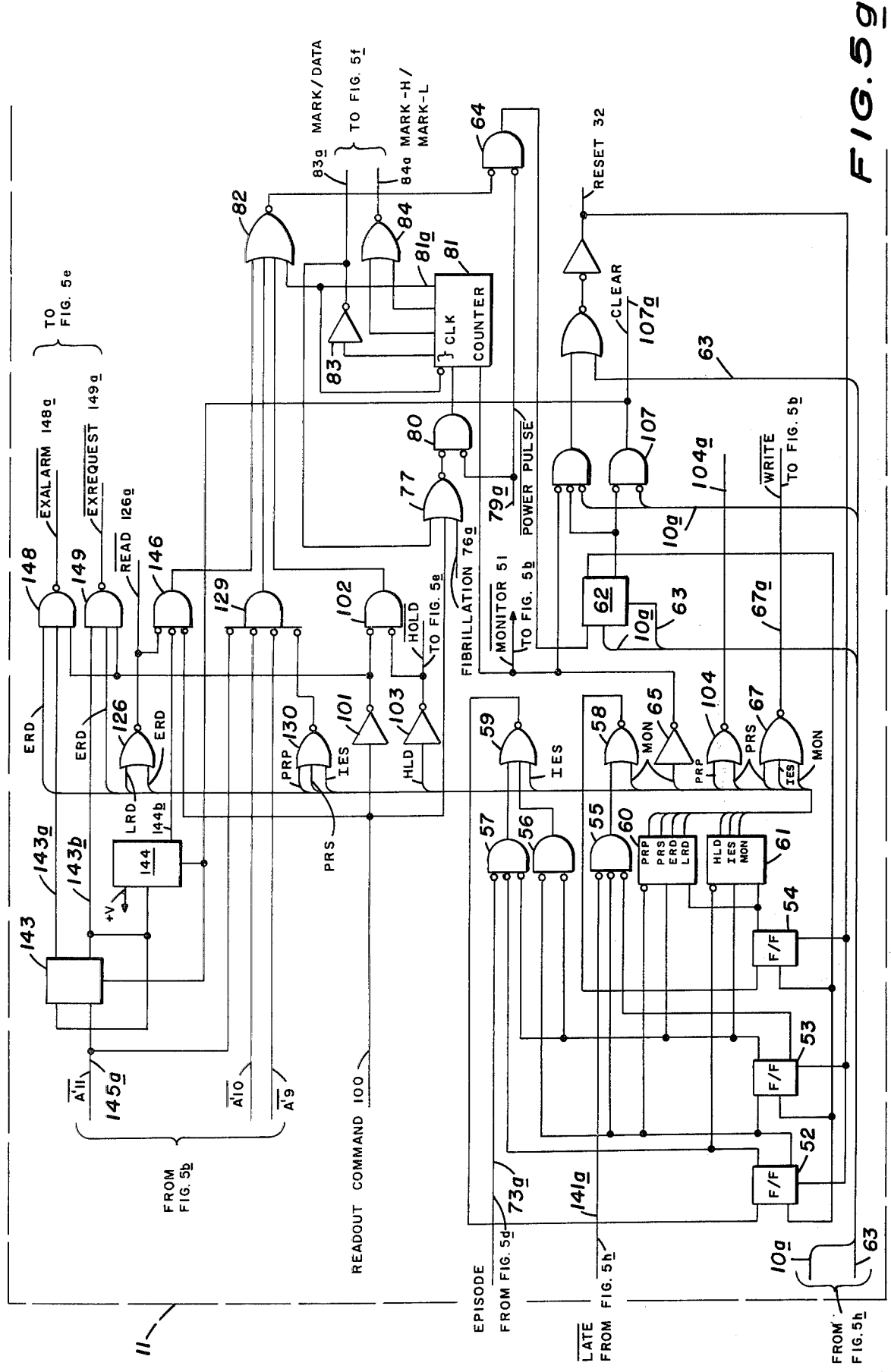

Referring to FIG. 5g of the drawings and the timing-/control circuitry, control over the operating state of the illustrated recorder implementation is provided by three flip-flop circuits 52, 53 and 54 and feedback control gates 55, 56, 57, 58 and 59. The seven output states or conditions corresponding to the nomenclature of FIG. 2 are thus demarcated or readout from the state control flip-flops 52, 53 and 54, as indicated on the output lines labelled MON, IES, HLD, LRD, ERD, PRS and PRP from decoders 60 and 61. The state control flip-flops 52, 53 and 54 are, in turn, controlled by a clocking flip-flop circuit 62 in response to the basic clock input from FIG. 5h on line 10a, a manual reset input on line 63 and the output of the AND gate 64 in FIG. 5g, as will now be described.

By way of example, when the proposed recorder system is in its MONITOR state (see FIG. 2) wherein it is sampling, A/D converting and storing the input analog ECG into the upper one-eighth of the RAM memory, as discussed previously in connection with FIG. 5b, the inverter 65 in FIG. 5g is producing a low control signal level on line 51 extending to FIG. 5b; thereby addressing, via the three OR gates 48, 49 and 50, the dedicated precursor portion of the RAM's 46a–f. Referring to FIGS. 2 and 5h, at the conclusion of each A/D conversion interval, as demarcated by the output of AND gate 36 in FIG. 5h, the RAM address counter 47 is clocked by the output of AND gate 66 through the one-eighth precursor portion of the RAM memory and thus provides continuously updated ECG data in storage. In FIG. 2, as noted earlier, the A/D sampling interval is illustrated as twenty miliseconds corresponding to the 50 Hz sampling rate; i.e. every twenty miliseconds, a new word of precursor ECG data is entered into the RAM memory. It should also be noted here that the RAM's 46a–f and the address counter 47 are trailing edge triggered units, so that each ECG data word is stored in memory at the trailing edge of the A/D START signal on line 34a (see FIG. 2) and the RAM address counter 47 is incremented on the trailing edge of the $\overline{\text{ADVANCE}}$ signal on line 66a. The storing or writing of the digital ECG data into memory 46a–f depends upon the $\overline{\text{WRITE}}$ signal on line 67a being low and this occurs when the OR gate 67 in FIG. 5g is enabled by the MON(i.e. MONITOR) output of state F/F decoder 61.

Referring again to FIG. 5h, with the illustrated recorder apparatus in its MONITOR condition as just described, the counter 70 is normally setting in a preset count state wherein output line 71 is in a high signal state. When fibrillation is detected, e.g. by the automatic implantable defibrillator (AID) unit as discussed above, a SHOCK PRECURSOR signal is received from the AID, on line 72 in FIG. 5h (see also FIG. 1), which resets the counter 70, so that the output line 71 now resorts to a low signal state (the EPISODE output signal on line 73a from the inverter 73 goes high) and gate 74 is rendered effective to apply clocking pulses from the clock divider 30 to the counter 70, at a rate which operates the counter 70 to return to its preset count condition in approximately forty seconds; i.e. the high signal level on line 73a and the corresponding low signal level on line 71 exists for approximately forty seconds following an initial occurrence of fibrillation and the receipt of a shock precursor signal on line 72.

Figure 3:
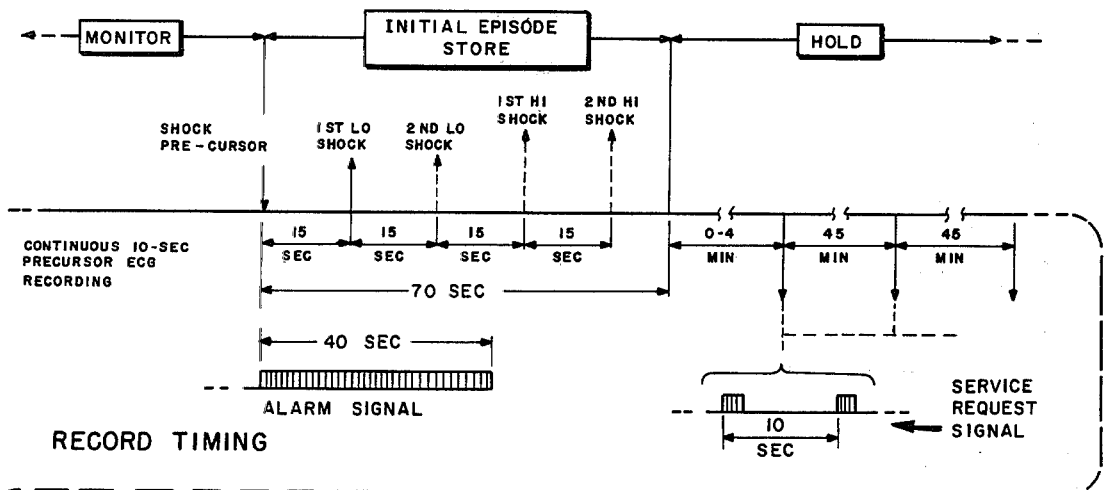
FIG. 3 is a timing diagram illustrating typical operation of the proposed recorder, involving various operating modes or states shown in FIG. 2.
Figure 3:
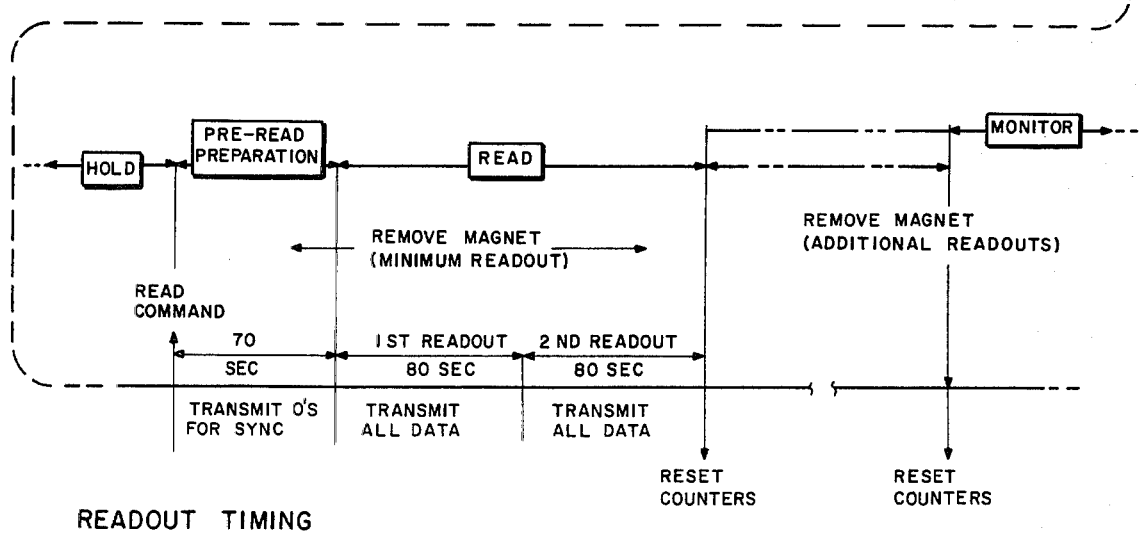

Referring now to FIGS. 2 and 3, this shock precursor signal actuates the recorder system to its INITIAL EPISODE STORE (IES) state. Specifically, when the counter 70 in FIG. 5h is reset from its normal preset count condition, the flip/flop circuit formed by interconnected OR gates 75 and 76 is triggered to produce a high signal level on line 76a and a low signal level on the output line 75a. The signal level on line 76a is applied to the OR gate 77 in FIG. 5g to enable the AND gate 80 to apply clock pulses from line 79a (at the 50 Hz rate and appearing at the end of the latent A/D conversion interval) to the counter unit 81. Subsequently, when the counter 81 reaches its counting state wherein the output line 81a is enabled, OR gate 82 enables the AND gate 64 and triggers F/F circuit 62 which controls clocking of the state flip-flop circuits 52, 53 and 54; i.e. the state flip-flops 52, 53 and 54 are now advanced one count, from the MONITOR state to the INITIAL EPISODE STORE state (see FIG. 2).

At this time, the IES output from the decoder 61 is applied to the OR gate 67 to again produce a low signal level on line 67a leading to FIG. 5b and comprising the write control for the RAM memory. This places the RAM's in condition to record digital ECG for a seventy second interval encompassing the defibrillation attempt. As previously discussed, the ECG data is sampled and digitized at a 50 Hz rate, under control of the A/D START signal appearing on line 34a between FIGS. 5h and 5f; i.e. once every 20 milliseconds, the ECG analog signal is converted to a digital word whose separate bits are applied to a corresponding RAM 46a, b, etc. of the memory and sequentially advanced through the main seventy seconds (e.g. lower) portion of the memory as the binary address counter 47 is clocked by the signal on line 66a.

The onset of fibrillation will, of course, occur at some random time in the sequencing of the precursor memory. To accommodate this, the circuitry shown in FIG. 5g comprising the inverter 83 and OR gate 84, connected to the output of the counter 81, supplies two marker signals on lines 83a and 84a to the analog ECG signal multiplexer 38 in FIG. 5f and insert a predetermined marker code in the precursor memory portion which marks where (in the memory) the onset of initial fibrillation episode occurs. This marker code enables a proper readout sequence for the ten seconds of precursor ECG data from storage.

PATIENT ALARM AND SERVICE REQUEST SYSTEMS

The illustrated embodiment of the recorder system includes a patient alarm generator unit 22, in FIG. 5e, whose purpose is to provide distinctive signals which both alert the patient when fibrillation has been detected (an "alarm") and advises the patient to seek medical attention following the defibrillation sequence (a "service request"). More specifically, the patient alarm and service request systems comprise AND gates 90 and 91 for selecting between the patient alarm and service request modes respectively, wherein the patient receives distinctive signal indications or stimuli; e.g. as two distinctive formats of stimulation current applied subcutaneously to cause a mild tickling sensation, and/or distinctive audible warnings, and/or temperature changes, and/or mechanical motions, etc.

More particularly, AND gate 90 is enabled by the normally high output from AND gate 94 (whose function will be described hereinafter in connection with patient training); the output of AND gate 92 which is connected to selected stages of the clock counter 30 (FIG. 5h) so as to produce low output pulse levels disposed forty milliseconds apart in time; and, the output of counter 70 (FIG. 5h) which, as previously described, produces a low signal level on line 71 upon the detection of a fibrillation condition. When the gate 90 is enabled by these three inputs, the OR gate 95 applies a continuous train of the pulses (spaced forty milliseconds apart) to a subcutaneous stimulation electrode 23 disposed, for example subcutaneously to provide a distinctive forty second interval of tickle stimulation to the patient (see FIG. 3), indicating that fibrillation has been detected and that a defibrillation sequence will soon be initiated. This form of subcutaneous electrical stimulation alerts the patient to the fact that unconsciousness will soon occur as a result of the fibrillation and that appropriate precautions should be taken; for example, if the patient is then driving a vehicle or is in any other potentially precarious situation.

Similarly, following successful defibrillation, the AND gate 91 is enabled by its three inputs, shown in FIG. 5e, to cause the OR gate 95 to apply two pulses (each approximately 1.3 seconds in duration and 10 seconds apart) every forty-five minutes to the patient; i.e. a "service request", until the patient seeks medical attention. Thus, the three inputs to the AND gate 91 are the forty millisecond spaced pulses from the AND gate 92; 1.3 second wide pulses spaced 10 seconds apart from the AND gate 93a connected to the counter 30 (FIG. 5h); and, output of AND gate 93 which is connected to the counter 31 so as to produce an output pulse once every forty-five minutes.

EVENT COUNTING

As previously noted, each time a shock precursor signal is received from the implanted defibrillator unit on line 72 in FIG. 5h, the counter 70 is reset and generates distinctive output signal levels on lines 71 and 73a. The signal on line 73a is applied to operate the episode counter 15 (see FIG. 5d) to store the total number of fibrillation episodes experienced by the patient between visits to the physician's office. Similarly, each time the shock precursor is received on line 72, from the AID apparatus preparatory to application of each defibrillation impulse, it also increments the shock counter 16 of FIG. 5d so that the doctor, upon readout, will be able to determine the total number of defibrillation impulses or shocks to which the patient was subjected since the patient's last visit.

As previously noted, the counter 17 in FIG. 5d registers time elapsed between the patient's last visit to the physician and the occurrence of the initial fibrillation event. Thus, when the signal level on line 75a at the output of the flip-flop circuitry 75–76 in FIG. 5h goes low, the gate 96 in FIG. 5d is disabled to terminate the counting operation of the counter 17, by blocking input clocking pulses from the gate 97 which occur every forty-five minutes, in response to the clock pulses applied thereto along line 97a from the timing/control circuitry of FIG. 5h. These forty-five minute clock pulses are output from the counter 31 and are derived by dividing down the basic 12.8 kHz clock signal. The same forty-five minute clock pulses at the output of gate 97 are continuously registered at 99, in the total elapsed time counter 18, to provide a registration of the total time (based on the forty-five minute increments) between the patient's visits to the doctor's office.

PHYSICIAN READOUT

A previously described, the six stage RAM memory 46a–46f shown in FIG. 5b provides, in storage, a digital representation of the patient's ECG, both for the ten second interval immediately preceding the initial fibrillation event and for the seventy second interval encompassing the fibrillation/defibrillation sequence. When the patient subsequently visits the physician, this ECG data is read out of storage, by the physician, in order to analyze the patient's cardiac activity which caused the defibrillator unit to operate, as well as the patient's response to the defibrillation attempt. Particularly, when the physician initiates a readout sequence, e.g. by placing a readout coil adjacent the implanted transmitter coil represented in FIG. 1, a readout command appears on line 100 in FIGS. 1 and 5g. This command signal is inverted, at 101 in FIG. 5g, and is applied to gate 102 along with the HLD signal which appears at the outputs of state decoder 61 and inverter 103 when the recorder system is activated to its HOLD state (see FIGS. 2 and 3) at the conclusion of the INITIAL EPISODE STORE (IES) state. As a result, gates 102, 82 and 64 are successively enabled (to allow the pulse on line 79a to enable the flip-flop 62) and the state control flip-flops 52, 53 and 54 are then controlled (by F/F 62) to advance from the HOLD state to the PRE-READ PREPARATION state (see FIG. 2) wherein a signal appears on line PRP from the decoder 60. This PRP signal enables the OR gate 104 in FIG. 5g which, in turn, applies an enabling signal level (line 104a) to the transmitter control gates 105 and 106, in the modulator/transmitter unit 21 of FIG. 5a, and renders the system of this invention effective to commence a communications sequence during which the contents of the RAM memory (digitized ECG) and the various event counters 15–18 (as well as the patient ID word 19) are transmitted, as will be described, to suitable external readout receiver apparatus of any conventional design located in the physician's office.

As shown in FIG. 1, the recorder system of the present invention is assumed to be implanted in the patient, along with the automatic defibrillator unit either in the same enclosure or in separate enclosures. Obviously, as an alternative, the proposed recorder system may be a battery-powered package carried externally by the patient, if desired. In such an application, the analog ECG signal and the defibrillation shock precursor signals would be coupled to the recorder by any suitable connection, e.g. by inductive pick-up through the patient's skin or by a direct percutaneous lead connector.

Referring to FIG. 3 of the drawings, during the seventy-seconds interval of the PRE-READ PREPARATION state, the illustrated implanted recorder embodiment initially transmits a sequence of binary zero's which allows synchronization between the external readout receiver apparatus and the recorder's internal clock rate. Towards the end of this sequence, a frame-synchronization modulation pattern is also generated to mark the beginning of real data. More specifically, in the timing/control circuitry of FIG. 5g, each time the output of flip-flop 62 demarcates a change in the operating state of the recording system, the gate 107 supplies a CLEAR signal on line 107a to the RAM address counter 47 in FIG. 5b. Accordingly, when the PRE-READ PREPARATION state is entered, the counter 47 begins cycling, at the twenty millisecond rate set by the clocking signal on line 66a, through the 12-bit address code on lines A0–A11. RAM readout, however, does not take place until the state control flip-flops 52–54 in FIG. 5g are actuated to the LATE READ state (see FIG. 2).

As the RAM address lines A0(LSB) through A11(MSB) are sequentially controlled to register the binary RAM address code, the AND gates 108 and 109 (FIG. 5a) generate a pair of gate signals $\overline{AG2}$ and $\overline{AG3}$ which are applied to gate 110 and control, along with other signal inputs to be described, the modulation pattern of the information transmitted by unit 21. In accordance with conventional binary code modulation techniques, the modulation pattern is assumed to be bi-level doublets in order that clocking fiducials may be imposed in the transmitted signal, along with the data. The $\overline{AG2}$ gate signal is also applied, along line 109a, to gate 111 in FIG. 5c, whose other input is connected to the A9 address line and whose output is connected to gates 112 and 113, along with the A2 and inverted A2 address signals respectively. The output is connected to gates 112 and 113, along with the A2 and inverted A2 address signals respectively. The output of gate 111 is also applied to the inhibit input of an ECG data multiplexer 114.

The outputs of gates 112 and 113 are a pair of gating signals $\overline{AG1}$ and $\overline{AG0}$ that are applied to and control enabling of a pair of decoder units 115 and 116 which convert or decode the A0 and A1 address line signals into a series of data outputting time slots $\overline{G0}$ through $\overline{G7}$, in accordance with the truth table shown in FIG. 7. As will be explained shortly, the $\overline{G0}$ through $\overline{G7}$ signals generated by decoders 115/116 control the selective multiplexing of the contents of the counters 15–18 and I.D. generator 19 into a serial output data stream (line QS in FIG. 5c) which is transmitted by the system. It is during the $\overline{G7}$ time slot that the signal level on line 115a is also effective to enable gate 106 in FIG. 5a and thereby impose the preselected frame-synchronization modulation pattern into the serial data stream, to mark the beginning of real data.

The B0, B1 and B2 clocking or control signals, generated on lines 30a by frequency divider 30 in FIG. 5h, provide bit selection control for multiplexing all data onto the data line QS; i.e., the B0(LSB), B1 and B2(MSB) bit signals are applied to and control, bit-by-bit, the transfer of data at each of the multiplexer units 114 and 120–125 illustrated in FIG. 5c. For example, when the recorder system is in its PRE-READ PREPARATION state, the high READ signal level on line 126a (from OR gate 126 in the timing/control circuitry of FIG. 5g) forces the outputs of gates 127 and 128 in FIG. 5c to a low (binary zero) state such that only the B0 bit select signal is effective to alternately connect the uppermost two grounded input lines to the QS data line. This produces a sequence of binary zero output data bits on the QS data line for approximately a seventy seconds interval during which multiplexer 114 is enabled by the output of gate 111 in response to a cycling of address counter 47 through the addresses corresponding to most of the lower or main seven-eighths of this RAM memory. As noted, this sequence of binary zero's are transmitted (see FIG. 3) to enable the external receiver apparatus to become synched to the output of the recorder system, as would be necessary for applications where the recorder is implanted along with the defibrillator unit.

Near the end of the seventy-seconds interval the G7 timing slot signal generated by decoder 115 in FIG. 5c (during the 8-word housekeeping interval shown in FIG. 7) is effective, through gate 106, to cause generation of the frame synchronization modulating pattern which demarcates the end of a transmission frame and, in this case, the onset of data.

Referring now to FIG. 5g and recalling that at the end of the seventy-second PRE-READ PREPARATION interval the address counter 47 is about to enter the precursor portion of the RAM memory (address lines A9, A10 and A11 will all be binary one), the gate 129 is enabled by the address line $\overline{A9}$, $\overline{A10}$ and $\overline{A11}$ and the output of OR gate 130. As a result, the OR gate 82 is enabled so that the next clocking pulse on line 79a is passed by gate 64 and sets up the flip-flop 62, to advance the state control flip-flops 52, 53 and 54 to the LATE READ state (see FIG. 2) wherein the LRD output of the decoder 60 is high. This LRD signal is applied to OR gate 126 and causes the signal level on line 126a to go low; thus enabling OR gate 105 in the modulator/transmitter circuitry of FIG. 5a and generating a transmitter gating interval during which the stored ECG data and the contents of the counters 14 through 18 and ID generator 19 are transmitted to the external receiver apparatus.

When the LATE READ state is entered, the AND gate 107 generates the CLEAR signal on line 107a extending to the RAM address counter 47 in FIG. 5b, as previously discussed. As a result, the address counter 47 again begins to cycle, at the 50 Hz rate fixed by the 20 millisecond spaced pulses on line 66a, through the 12-bit address code A0–A11. Beginning with the first RAM address in the main memory portion, each of the six-bit words contained in the memory is sequentially outputted on lines Q0 through Q5 to the ECG data multiplexer 114 (FIG. 5c) and subsequently applied bit-by-bit, in serial format, along line Q5 to the modulator/transmitter circuitry in FIG. 5a. Here, each data word is AND'ed (at 131) with the output of binary counter/shift register 132 to generate a distinctive binary data modulation pattern.

The sequential readout of the first or lower 7/8's main portion of the RAM memory (seventy seconds of post-fibrillation ECG) continues until the last eight word section of the main RAM portion is reached (see FIG. 7), at which time the output of AND gate 111 in FIG. 5c inhibits the RAM multiplexer 114. During the ensuing eight word interval, the housekeeping data comprising the readout from the various counters 15–18 shown in FIG. 5d and the I.D. generator 19 are multiplexed to the modulator/transmitter 21 (see FIG. 5a) for communication to the external receiver equipment. More specifically, during readout, the counters 15–18 are sequentially multiplexed, by multiplexers 121–125 respectively, onto the QS data line by the $\overline{G0}$ through $\overline{G4}$ timing signals produced by decoders 115/116 in FIG. 5c; whereas, during timing slots $\overline{G5}$, $\overline{G6}$ and $\overline{G7}$, the multiplexer 120 repeats three successive ID words from the generator 19 onto the QS data line. If desired, e.g. in order to expand the other housekeeping data, only one ID word can be transmitted. As noted earlier, during the final timing slot $\overline{G7}$ in the eight word housekeeping interval, the transmitted data stream also contains the frame synchronization modulation pattern.

At this point in time, the RAM address counter 47 in FIG. 5b begins to address the remaining one-eighth (10 seconds) of the RAM memory containing the ECG data for the patient immediately preceding the onset of fibrillation. This precursor ECG data is thereupon read out through the multiplexer 114, in FIG. 5c, which is now enabled by the removal of the inhibiting control signal at the output of AND gate 111. When the RAM memory has been completely read out, the control signals at the outputs of AND gates 108 and 109 in FIG. 5a are both true, to enable AND gate 110 and thereby inject the previously mentioned modulation pattern into the output transmitted data as a frame synchronization marker.

As previously noted and as shown in FIG. 2, if the patient, upon application of a readout command 100 (in FIG. 5g), has not experienced a fibrillation since the last visit to the physician, the readout command places the recorder system in the PRE-READ STORE state rather than PRE-READ PREPARATION. Thus, in the timing/control circuitry of FIG. 5g, it will be noted that, receipt of the readout command on line 100 is effective, through OR gate 77 and gate 80 to allow the pulses on line 79a to clock the counter 81. Consequently, a marker code is inserted in the precursor memory portion, similar to the code abled to effectuate a change, in the state control flip-flops 52–54, from the MONITOR to the PRE-READ STORE state. As a result of this state change, the signal on line 107a clears the RAM address counter 47 and initiates cycling through the main seven-eithths portion of the memory, at the 50 Hz rate, to store the patient's current ECG, following A/D conversion thereof as previously described.

In a manner similar to that described previously when discussing the PRE-READ PREPARATION state, during the PRE-READ STORE state the recorder system transmits seventy seconds of binary zeros, to synchronize the receiver apparatus to the clock rate of the recorder; i.e. the OR gates 104 and 105 in FIGS. 5g and 5a respectively are each enabled during the PRE-READ STORE state to gate on the transmitter circuitry. At the conclusion of the seventy seconds interval of the PRE-READ STORE state (when the RAM address counter enters the upper one-eighth of the memory), the operation of the gating circuits 129, 82 and 64 in FIG. 5g causes the recorder system to advance to the LATE READ state, as previously discussed. During this state, the ECG data just stored will be readout, through multiplexer 114, as a serial data stream (on line QS) followed by the contents of the counters 15–18, I.D. word generator 19, and the precursor ECG data.

Referring to FIG. 5h, the selection between the EARLY and LATE READ states is controlled by the output on line 140a from the clock divider unit 31 and the flip-flop formed by interconnected OR gates 141 and 142 (see FIG. 5h) which produces a low signal on line 141 approximately ten minutes after the recorder system enters the MONITOR state. Thus, if the physician reinitiates an interrogate or readout command within ten minutes of an earlier readout operation, the signal level on line 141a causes the state control flip-flops 52–54 in FIG. 5g to enter the EARLY READ state (ERD); whereas, if at least ten minutes has elapsed between the readout operations, the recorder enters the normal or LATE READ (LRD) state.

Referring once again to the readout timing diagram of FIG. 3, it should be noted that the proposed recorder system provides a minimum of two readouts, in the event that the readout coil is removed immediately following communication of a readout command. This two-readout minimum is assured by the operation of the flip-flops 143 and 144 in FIG. 5g. More particularly, the leading edge of the $\overline{A11}$ signal on control line 145a, from the address counter 47 in FIG. 5b, supplies a toggling input to the flip-flop 143 at the end of the first readout operation. As a result, the flip-flop output line 143a goes true (high) at the end of the first readout operation and remains in this state during the second readout operation. Conversely, the other output line 143b from the flip-flop 143 is high during the first readout operation, goes low during the second readout operation, and returns to high at the end of the second readout operation. The flip-flop unit 144, also being a leading edge-triggered unit, is therefore toggled and its output line 144b goes low only at the end of the second readout operation. Moreover, the flip-flop 144 will remain in this state until it is reset by the CLEAR signal at the output of AND gate 107, when the state control flip-flops 52–54 are clocked from a READ to the MONITOR state. This particular state change is controlled to occur when the output of the AND gate 146 in FIG. 5g goes high; i.e. when the readout command is absent from line 100, the output line 144b of flip-flop 144 is low, and the output of OR gate 126 is also low to indicate that the recorder system is in a READ state. Thus, as long as a readout command is present on line 100, the gate 146 is disabled (to prevent a change from the READ state) and readouts continue so long as the readout command signal is present; whereas, when the readout coil is removed, the state change to MONITOR is deferred until two readout cycles take place.

PATIENT TEST

In order to acquaint the patient with the "alarm" and (go-see-the-doctor) "service request" alert signals provided during operation of the proposed recorder system, provision is made in the illustrated embodiment whereby the physician can simulate these two alert signals; e.g. by placing the readout command coil in position and then removing it right away. More particularly, upon removal of the readout command coil in a manner to induce the EARLY READ state just described, the high signal levels appearing successively on lines 143b and a from the flip-flop unit 143 (FIG. 5g) successively enable the AND gates 149 and 148 respectively. The true output from AND gate 149 is applied, over line 149a, to the input of AND gate 150 (in the patient stimulator of FIG. 5e). along with the address line signals $\overline{A6}$, $\overline{A7}$, $\overline{A8}$, $\overline{A10}$, and $\overline{A11}$ from the RAM address counter 47 in FIG. 5b. As a result, the output of AND gate 150 is a pair of 1.25 second long pulses spaced ten seconds apart which are applied through the OR gate 95 to simulate the service request alert which, as previously described, occurs after the patient has undergone a defibrillation sequence and is being alerted to visit his/her physician immediately. Similarly, the signal on line 148a at the output of AND gate 148 in FIG. 5g l is applied, along with the address signal line A11, to the AND gate 151 in FIG. 5e which responds by generating a forty second signal pulse input to OR gate 95, to simulate the "alarm" signal alert which is given to the patient at the onset of ventricular fibrillation.

Although not disclosed in detail herein, the receiver apparatus located in the physician's office can be of any suitable design to receive and decode the serial data bit stream transmitted by the recorder system, and then display it as desired. This would involve simply dividing up the serial data bit stream properly, into the eight bit increment or word format employed for transmitting both the ECG data from the RAM memory and the housekeeping data supplied by the various counters and the device identification number generator included within the recorded system. It should also be understood that, as previously noted, the principles of the proposed recording system are equally applicable to an externally located recorder and that, in such a case it would be unnecessary to utilize separate receiver equipment. In other words, the ECG data could readily be outputted directly to a suitable D/A converter and then displayed (e.g. on a strip chart) and the housekeeping data could be applied directly to suitable visual displays (e.g. utilizing LED alphanumerics).

Various other modifications, adaptations and alterations are of course possible in light of the above teachings. It should therefore be understood at this time that within the scope of the appended claims, the invention may be practiced otherwise than as specifically described hereinabove.

What is claimed is:

1. A recorder system, adapted for use with an automatic defibrillator system responsive to a patient's electrocardiagram (ECG) data and capable of detecting the occurrence of abnormal cardiac activity and render effective automatically in response thereto to generate and apply one or more defibrillation electrical impulses to the patient's heart intended to return the heart to normal functioning, said recorder system being responsive to the patient's ECG data and comprising, in combination, means for sampling and converting said ECG data from analog to digital form, first and second ECG data digital storage means, means for registering the occurrence of said abnormal cardiac activity as detected by said automatic defibrillator system, storage control means controlled by said occurrence registering means responsive to the occurrence of said abnormal cardiac activity for selectively rendering effective said first and second ECG data storage means to store ECG digital data occurring respectively for a first time period just prior to the occurrence of said abnormal cardiac activity or for a second time period encompassing the application of said defibrillation impulse(s) by said automatic defibrillator system, time registration means controlled by said occurrence registering means responsive to the occurrence of said abnormal cardiac activity for registering as a digital code the time of occurrence of said abnormal cardiac activity, first counting means responsive to the generation of each defibrillation impulse by said automatic defibrillation system for registering as a digital code a count of the number of said defibrillation electrical impulses generated by said automatic defibrillator system, second counting means responsive to said occurrence registering means for registering as a digital code a count of the number of occurrences of said abnormal cardiac activity, and readout control means operable upon command for reading out
  (a) the ECG digital data stored in each of said first and second storage means,
  (b) the digital code time registration of said time registration means, and
  (c) the digital code counts of each of said first and second counting means.

2. The recorder system specified in claim 1 wherein: said means for sampling and converting the patient's analog electrocardiogram (ECG) signal generates a succession of corresponding digital data words, and said first and second ECG digital data storage means includes memory means subdivided into a first portion updated continuously to store the digital code words corresponding to a preselected first ECG interval prior to the operation of said defibrillator, and a second portion to store the digital code words corresponding to a second preselected ECG interval encompassing the operation of said defibrillator and indicating the patient's response to said defibrillation electrical impulse(s).

3. The recorder system specified in claim 1 further including means rendered effective upon the occurrence of said abnormal cardiac activity to provide a first alarm warning signal to the patient indicating said occurrence and rendered effective following operation of said automatic defibrillator to provide a second service request warning signal to the patient indicating that said automatic defibrillator has operated.

4. The recorder system specified in claim 3 wherein said first and second warning signals each have unique characteristics rendering them distinguishable from one another by the patient.

5. The recorder system specified in claim 4 including means for repeating said second warning signal at selected intervals for continuously reminding the patient to seek medical assistance.

6. The recorder system specified in claim 3 further including means controlled by the patient's physician for selectively commanding said first alarm and second service request warning signals, as desired.

7. The recorder system specified in claim 1 further including means to reset each of said time registration means and said first and second counting means following readout.

8. The recorder system specified in claim 1 wherein said recording system is implanted and further including communications means comprising:

an external transmitter means for transmitting a readout command an implanted means for receiving said readout command to initiate operation of said read out control means, an implanted transmitter means for transmitting a digital signal including said read out ECG digital data, said digital code time registration and said digital code counts, and an external receiver means for receiving said transmitted digital signal.

9. The recorder system specified in claim 8 wherein said recorder system further includes means for specially encoding the transmission to said external receiver means for each particular patient.

10. The recorder system specified in claim 8 wherein said recorder system further includes means rendered effective upon transmission of said readout command to apply a predetermined digital code to said internal transmitter means to initiate transmission by said implanted transmitter means of a predetermined transmission pattern preceding the transmission of said stored data for synchronizing said external receiver means to said data transmission.

11. The recorder system specified in claim 8 further including means for controlling said internal transmitter means to transmit said data at least twice each time a readout command is transmitted.

12. The recorder system specified in claim 11 including means to control said internal transmitter means to continuously transmit said data so long as a readout command is continuously transmitted.

13. The recorder system specified in claim 8 further including multiplexer means connected to said implanted transmitter means for multiplexing said ECG digital data, said digital code time registration and said digital code counts into a serial data output bit stream for transmission.

14. The recorder system specified in claim 13 further including:
  clocking means for establishing the data bit rate for said data output bit stream,
  means responsive to said clocking means for generating a predetermined bit pattern, and
  means rendered effective upon transmission of a readout command to initiate transmission of said predetermined bit pattern prior to transmission of said serial data output bit stream for synchronizing said external receiver means to the data bit rate of said data output bit stream.

15. The recorder system specified in claim 14 further including implantable code generator means for producing a code signal distinctively identifying the particular patient in which the recorder system is implanted, and means for incorporating said patient identifying code signal into said serial data output bit stream.

16. The recorder system specified in claim 13 further including means for adding to said serial data output bit stream a digital code identifying the particular patient whose ECG signal is represented by said serial data output bit stream.

17. A recorder system responsive to a selected physiological signal of a patient for monitoring, storing and reading out, on command, data regarding a particular physiological functioning represented by said physiological signal for that patient, comprising:
  means for sampling and converting said physiological signal from an analog form into a corresponding digital data signal format, addressable memory means for storing the digital data signal, said memory means being divided into first and second storage portions, means for repeatedly addressing the first storage portion of said memory prior to the occurrence of a preselected physiological event to continually update the digital data stored in said first storage portion, means for registering the occurrence of said preselected physiological event, means controlled by said registration means rendered effective upon the occurrence of said preselected physiological event to hold the most recent digital data then stored in said first storage portion corresponding to a first predetermined interval preceding said event, means controlled by said registration means rendered effective upon the occurrence of said preselected physiological event for thereafter addressing the second storage portion of said memory to store the digital data corresponding to said physiological signal during a second predetermined interval following said event, readout control means operable upon command for reading out the digital data stored by said first and second storage portion of said memory, means for commanding said readout control means, and patient identification generator means responsive to said readout control means for annexing a code to said digital data during readout uniquely identifying the particular patient.

18. The recording system specified in claim 17 wherein said converting means converts said physiological signal from an analog form to a succession of multiple bit digital data words and wherein said addressable memory means comprises a plurality of random access memory (RAM) stages.

19. The recording system specified in claim 17 wherein said commandable readout control means includes multiplexing means for arranging the stored digital data bits into a serial data output bit stream during readout.

20. The recording system specified in claim 19 wherein said sampling and converting means, said memory means and said multiplexing means of the recording system are implanted in the patient's body and wherein said commandable readout control means comprises an internal receiver means and an external transmitter means for communicating an externally selected readout command signal to the implanted receiver means, and further including an external receiver means and an implanted transmitter means rendered effective following communication of said readout command for transmitting said serial data output bit stream to said external receiver means.

21. The recorder system specified in claim 17 further including means rendered effective upon the occurrence of said preselected physiological event for providing a distinctive warning signal to the patient indicative of said event occurrence.

22. The recorder system as specified in claim 17 further including timing means and means for resetting said timing means, said timing means being responsive to the occurrence of said preselected physiological event for providing a registration of selected time interval information of interest in analyzing the patient's physiological functioning represented by said physiological signal.

23. The recorder system specified in claim 22 wherein said timing means comprises a source means for generating time clocking pulses and said resetting means comprises resettable pulse counter means connected to said source means, said timing means being responsive to said physiological signal for registering a running count of the number of time clocking pulses to demarcate said selected time interval information.

24. A recorder system specified in claim 23 wherein said time interval information includes the time interval between the patient's last readout and said event occurrence.

25. The recorder system specified in claim 24 further including event counter means responsive to said physiological signal for registering a count of the number of said physiological events occurring between readouts.

26. The recorder system specified in claim 25 wherein said signal sampling and converting means, said memory means, said pulse counter means and said event counter means are implanted in the patient's body and further including:
implanted multiplexing means for arranging the data stored in said memory means and the count registrations of said pulse and event counter means into a serial bit stream format,
external display apparatus, and
implanted transmitter means operably connected to said multiplexing means for transmitting said serial bit stream to said external apparatus for display.

27. The recorder system specified in claim 26 wherein said implanted mulitplexing means comprises:
an output data line connected at one end to said implanted transmitter means,
a plurality of multiplexer units, one of which is connected to receive as input the contents of an associated one of said data memory means and said pulse and even counter means,
the other end of said output data line being connected in parallel to the output of each of said plurality of multiplexer units, and
timing means for sequentially rendering effective said plurality of multiplexer units to apply the contents of the associated data memory means or pulse and event counter means to said other end of the output data line.

28. The recorder system specified in claim 26 further including
means for inserting said patient-identifying code into said serial bit stream.

29. A recorder system for use with an automatic defibrillation system implanted in a patient and operable, in response to the detection of abnormal cardiac activity, to apply automatically defibrillation electrical impulse to the patient's heart in an attempt to correct said abnormal activity if such activity continues for longer than a predetermined time interval, said recorder system being responsive to the patient's electrocardiagram (ECG) signal and comprising, in combination:
means for registering the detection of said abnormal cardiac activity,
means for registering completion of a corrective attempt by said implanted automatic defibrillation system,
storage means for storing said ECG signal for a time period of interest extending substantially from the time at which said abnormal cardiac activity is detected to a predetermined time following application of said defibrillation electrical impulse by said implanted automatic defibrillation system;

means for reading out the ECG signal stored by said storage means, and patient warning means for providing the patient with distinctive warnings of the occurrence of said abnormal cardiac activity and the responsive operation of said implanted automatic defibrillator system, said patient warning means including warning signal generating means implanted in the patent responsive to the detection of said abnormal cardiac activity and the responsive application of said electrical impulse by said implanted automatic defibrillation system for generating first and second patient stimulus signals respectively; and means responsive to said first and second patient stimulus signals for converting said first and second patient stimulus signals each to a different distinctive from detectable by the patient to warn the patient of said abnormal cardiac activity and said responsive defibrillation respectively.

30. The implanted patient warning system specified in claim 29 wherein said means for generating said first and second patient stimulus signals comprises a source of electrical pulses and wherein said converting means comprises subcutaneous electrode means connected to be energized by said electrical pulse and producing a patient tickling sensation.

31. The implanted patient warning system specified in claim 26 wherein said warning signal generating means generate first and second patient stimulus signals comprising electrical pulses grouped in first and second distinctive time patterns, and wherein said converting means comprises subcutaneous energizable electrode means connected to be energized by said electrical pulses to produce patient tickling sensations enabling said patient to distinguish between (a) the detection of said abnormal cardiac activity and (b) the completion of said corrective attempt by said implanted automatic defibrillation system.

32. A recorder system responsive to a selected physiological signal of a patient for recording said physiological signal comprising, in combination, means for periodically converting samples of said physiological signal into a succession of digital data code words, means for registering the occurrence of a preselected event in said physiological signal, memory means including a plurality of random access memory (RAM) stages capable of storing said digital data code words at selected addresses within said memory means, memory address control means responsive to said registering means for selectively addressing the RAM stages of said memory to (a) store digital data code words corresponding to a first predetermined time interval of said physiological signal immediately preceeding said preselected event in a first portion of said memory comprising memory addresses corresponding to said first predetermined time interval, and (b) store digital data code words corresponding to a second predetermined time interval of said physiological signal following said preselected event in a second portion of said memory comprising selected other memory addresses, said memory address control means including means for generating address selecting signals to sequentially address all memory addresses and logic circuit means connected to said generating means for (a) forcing said generating means to generate address selecting signals which repeatedly address in sequence said selected memory addresses corresponding to said first memory portion until said preselected event occurs in said physiological signal, and (b) thereafter enable generation of address selecting signals which address in sequence the other memory addresses corresponding to said second memory portion, and means for reading out the digital data code words from said memory means.

33. The recorder system specified in claim 32 further including marker means responsive to said registering means for generating a marker code signal to demarcate the address in said first memory portion corresponding to the occurrence of said preselected event.

34. The recorder system specified in claim 32 wherein said readout means includes a data output line and further including means for registering selected housekeeping data and means responsive to said memory address control means for multiplexing said housekeeping data with said data code words onto said data output line during readout.

* * * * *